United States Patent [19]
Nields et al.

[11] Patent Number: 6,102,866
[45] Date of Patent: Aug. 15, 2000

[54] ENHANCED BREAST IMAGING/BIOPSY SYSTEM EMPLOYING TARGETED ULTRASOUND

[75] Inventors: Morgan W. Nields, Englewood; Bogdan R. Ulatowski, Westminster, both of Colo.

[73] Assignee: Fischer Imaging Corporation, Denver, Colo.

[21] Appl. No.: 09/111,094

[22] Filed: Jul. 6, 1998

Related U.S. Application Data

[63] Continuation-in-part of application No. 08/730,107, Oct. 15, 1996, Pat. No. 5,776,062.

[51] Int. Cl.⁷ ..................................................... A61B 8/00
[52] U.S. Cl. .......................... 600/461; 600/407; 128/915; 128/916
[58] Field of Search .................................... 600/407, 417, 600/424, 427, 429, 437, 439, 443, 461; 378/37, 209; 128/915–916

[56] References Cited

U.S. PATENT DOCUMENTS

| | | | |
|---|---|---|---|
| 2,707,662 | 5/1955 | Goldfield et al. | 311/6 |
| 3,165,630 | 1/1965 | Bielat et al. | 250/58 |
| 3,963,933 | 6/1976 | Henkes, Jr. | 250/456 |
| 3,973,126 | 8/1976 | Redington et al. | 250/444 |
| 4,051,380 | 9/1977 | Lasky | 250/451 |
| 4,099,880 | 7/1978 | Kano | 356/164 |
| 4,249,539 | 2/1981 | Vilkomerson et al. | 128/662.05 |
| 4,341,120 | 7/1982 | Anderson | 73/618 |
| 4,346,717 | 8/1982 | Haerten | 128/660 |
| 4,485,819 | 12/1984 | Igl | 128/660 |
| 4,567,896 | 2/1986 | Barnea et al. | 128/662.05 |
| 4,576,175 | 3/1986 | Epstein | 128/662.05 |
| 4,613,122 | 9/1986 | Manage | 269/322 |
| 4,618,973 | 10/1986 | Lasky | 378/37 |
| 4,625,555 | 12/1986 | Fujii | 73/597 |
| 4,671,292 | 6/1987 | Matzule | 600/461 |
| 4,727,565 | 2/1988 | Ericson | 378/205 |
| 4,750,487 | 6/1988 | Zanetti | 128/303 |
| 4,791,934 | 12/1988 | Brunnett | 128/653 |
| 4,869,247 | 9/1989 | Howard, III et al. | 128/303.1 |
| 4,875,478 | 10/1989 | Chen | 128/303 B |
| 4,890,311 | 12/1989 | Saffer | 378/99 |
| 4,899,756 | 2/1990 | Sonek | 600/461 |
| 4,930,143 | 5/1990 | Lundgren et al. | 378/37 |
| 5,078,142 | 1/1992 | Siczek et al. | 128/653.1 |
| 5,129,911 | 7/1992 | Siczek et al. | 606/130 |
| 5,285,772 | 2/1994 | Rattner | 128/24 E |
| 5,289,520 | 2/1994 | Pellegrino et al. | 128/662.05 |
| 5,320,111 | 6/1994 | Livingston | 128/754 |
| 5,398,690 | 3/1995 | Batten et al. | 128/662.05 |
| 5,409,497 | 4/1995 | Siczek et al. | 606/130 |
| 5,411,026 | 5/1995 | Carol | 128/660.03 |
| 5,415,169 | 5/1995 | Siczek et al. | 128/653.1 |
| 5,426,685 | 6/1995 | Pellegrino et al. | 600/429 |
| 5,447,154 | 9/1995 | Cinquin et al. | 127/653.1 |
| 5,474,072 | 12/1995 | Shmulewitz | 128/660.09 |
| 5,479,927 | 1/1996 | Shmulewitz | 68/915 |
| 5,499,630 | 3/1996 | Hiki et al. | 600/461 |
| 5,526,394 | 6/1996 | Siczek et al. | 378/37 |
| 5,569,266 | 10/1996 | Siczek | 606/130 |
| 5,584,292 | 12/1996 | Cheung | 128/653.1 |
| 5,647,373 | 7/1997 | Paltieli | 600/461 |
| 5,660,185 | 8/1997 | Shmulewitz et al. | 128/437 |

FOREIGN PATENT DOCUMENTS

WO 83/02053  6/1983  WIPO.

OTHER PUBLICATIONS

Jan Bolmgren, Bertil Jacobson and Bjorn Nordenstrom, "Stereotaxic Instrument for Needle Biopsy of the Mamma" J Roenigenol 129:121–125, Jul. 1977.

*Primary Examiner*—Francis J. Jaworski
*Attorney, Agent, or Firm*—Holme Roberts & Owen LLP

[57] ABSTRACT

The present invention provides for x-ray imaging and ultrasound imaging of a body region of interest in a spatially correlatable manner. The resultant x-ray and ultrasound images may be combinatively employed to provide three-dimensional information regarding a location of interest within the body, and is particularly apt for use in the analysis/biopsy of potential lesions and suspicious masses in a female breast. The invention provides for direct body contact by an ultrasound imaging head, as well as targeted ultrasound imaging of a selected portion of the region from which x-ray images are obtained.

22 Claims, 8 Drawing Sheets

ENHANCED BREAST IMAGING/BIOPSY SYSTEM EMPLOYING TARGETED ULTRASOUND

RELATED APPLICATIONS

This application is a Continuation-In-Part of U.S. parent application Ser. No. 08/730,107 entitled "ENHANCED BREAST IMAGING/BIOPSY SYSTEM EMPLOYING TARGETED ULTRASOUND", filed Oct. 15, 1996 and in U.S. Pat. No. 5,776,062.

FIELD OF THE INVENTION

The present invention relates to medical imaging/biopsy systems, and more particularly, to an enhanced system that employs x-ray imaging and targeted ultrasound imaging in a combinative, spatially correlatable manner that is particularly apt for breast imaging/biopsy procedures. The invention further relates to targeted ultrasound features that yield plural modalities of operation as well as improved biopsy capabilities.

BACKGROUND OF THE INVENTION

The benefits of early detection and tissue diagnosis of potential lesions and/or suspicious masses within the body is now well established. Indeed, as medical practice and managed care plans continue to evolve, the role of early detection and tissue diagnosis is ever-increasing. With such emphasis, both efficacy and efficiency are at a premium. Specifically, reduction of the time requirements of highly trained medical personnel, patient office visits and medical equipment costs (e.g., via use of multiple-purpose equipment) are primary objectives for procedures utilized in the early detection and tissue diagnosis of potential lesions and otherwise suspicious masses.

Of particular ongoing interest is the area of mammography and breast biopsy. Currently, it is common for patients to receive regular screening mammograms, wherein two x-ray images are generated for each breast in order to identify potential lesions or masses suspicious for malignancy. In the event of equivocal screening mammograms, further x-ray or ultrasound imaging/exams may be performed to obtain additional information. The obtainment of a diagnostic mammogram and/or an ultrasound exam requires another patient office visit and additional medical personnel time. For example, if the presence of a suspicious mass is confirmed, an ultrasound procedure is performed in order to further characterize the mass. Specifically, a free-hand procedure is performed in which a hand-held ultrasound probe is manipulated on the breast while viewing a display to obtain depth-profile information. As can be appreciated, location of a potential lesion/suspicious mass can be difficult, and the ultrasound images obtained are frequently difficult to mentally associate with the x-ray images. As such, the ability to utilize ultrasound technologists as opposed to experienced physician specialists to perform most breast ultrasound procedures is limited.

Should a breast lesion show signs of malignancy pursuant to diagnostic mammography or ultrasound, a breast biopsy is typically performed. Needle localized surgical biopsy means have recently been giving way to stereotactic x-ray biopsy with automated core needles and tissue removal systems. A patient is typically positioned prone (e.g., on a solid table) with the breast immobilized within a predetermined frame of reference (e.g., the breast passes through an opening in the table and is immobilized between opposing compression plates). Stereotactic X-ray images are then generated (e.g., via x-ray film or digital imaging) for review by medical personnel to identify a specific location of interest (e.g., corresponding with a potential lesion or suspicious mass) within the predetermined frame of reference. A puncture instrument, mounted in predetermined relation to the predetermined frame of reference, is then positioned/utilized to obtain a sample of tissue from the location of interest. Of note, current state-of-the-art breast biopsy systems include the MAMMOTEST®, MAMMOVISION® and SENOSCAN™ products offered by Fischer Imaging Corporation of Denver, Colo. Such systems are further described in U.S. Pat. Nos. 5,078,142, 5,240,011, 5,415,169, 5,526,394 and 5,735,264, hereby incorporated by reference in their entirety.

While all breast lesions may typically be biopsied utilizing stereotactic x-ray imaging, only recently have technical improvements in ultrasound allowed certain lesions to be biopsied under ultrasound guidance (i.e., with hand-held ultrasound probe and/or biopsy means). In this regard, ultrasound may be preferred due to the lack of ionizing radiation and the established availability of real time imaging to reduce procedure time.

Recent developments in tissue removal systems have resulted in larger, heavier devices that are difficult for a physician to use in conjunction with free-hand ultrasound guidance. As an example, the MAMMOTOME™ from Biopsys Medical, Inc. of Irvine, Calif. allows rapid removal of breast tissue through a small puncture hole in the breast. Due to the weight and size of the device, physicians are performing more stereotactic x-ray procedures with the MAMMOTOME™ due to the solid support of the device by prone stereotactic tables.

In the event that analysis of tissue by histopathologic techniques indicates that a lesion or undesirable mass should be removed from a breast, the surgeon will typically review the various breast images previously obtained to develop a therapeutic surgical strategy, with the goal of removing the entire potential lesion and/or suspicious mass while achieving acceptable cosmetic results.

SUMMARY OF THE INVENTION

It is an object of the present invention to provide an enhanced imaging/biopsy system that can reduce trained medical personnel time requirements in diagnostic and biopsy procedures for tissue diagnosis. It is a related objective to provide such a system in a cost-effective manner; namely through the provision of a system having relatively expensive components that can be utilized for multiple medical procedures combinatively employed in a single system.

A further objective of the present invention is to provide an enhanced imaging/biopsy system for obtaining spatially correlated three-dimensional image information regarding a location of interest in the body, such system being apt for the obtainment of three-dimensional image information regarding a potential lesion or suspicious mass in a female patient's breast. It is a further objective to provide such information in a manner allowing for enhanced use of tissue removal systems used for obtaining tissue samples from the body, including specifically, tissue from a potential lesion or suspicious mass within a female patient's breast.

Yet another objective of the present invention is to provide an enhanced imaging/biopsy system for obtaining depth-related image information for diagnostic use and for otherwise yielding biopsy-related control and access advantages.

These objectives and additional advantages are met by various aspects of the present invention. In this regard, one aspect of the present invention provides for the combinative use of x-ray imaging and targeted ultrasound imaging. More particularly, this inventive aspect provides for the transmission of x-ray radiation through a selected body region-of-interest within a predetermined, three-dimensional frame of reference to obtain x-ray image data corresponding with one or more x-ray images. Additionally, an ultrasound signal is directed into a limited, selectively targeted portion of the x-rayed body region of interest to provide ultrasound image data corresponding with one or more ultrasound images of the targeted portion of the selected body region. The x-ray and ultrasound image data are acquired in spatial co-relation by utilizing x-ray imaging means and ultrasound imaging means each supportably positioned in known co-relation to the predetermined, three-dimensional frame of reference. This arrangement allows the x-ray and ultrasound image data to combinatively provide correlated, three-dimensional image data corresponding with the body region of interest. In turn, the spatially correlated information allows for an enhanced medical diagnosis of a given location of interest within the body region (e.g., potential lesion or suspicious mass in a breast application) and enhanced biopsy options in relation thereto.

In an additional aspect of the present invention, an ultrasound imaging means is provided that is advantageously positionable in direct contact with the body region of interest for optimal ultrasound image acquisition. More particularly, in breast imaging applications, opposing compression plates may be employed to immobilize a patient's breast within the predetermined, three-dimensional frame of reference, wherein an opening is provided in one of the compression plates for selectively positioning an ultrasound imaging head (e.g., comprising a linear ultrasound transducer array) therethrough in contact with the patient's breast for imaging. The ultrasound imaging means may be positioned below and on either side of a center axis of a patient support table, or alternatively, may be positioned below and in substantially coaxial relation to a patient support table.

In another aspect of the present invention, a locating means (e.g., an image data processor with display/user interface) is provided for using x-ray and ultrasound image data to identify a particular location of interest within the body region of interest; and a biopsy means is provided for obtaining a sample from the identified location of interest. In this regard, the biopsy means may include positioning means for selectively and supportably positioning an elongated puncture instrument or other tissue removal system relative to the predetermined, three-dimensional frame of reference, including for example positioning at a desired entry angle.

In a further aspect of the present invention, an ultrasound imaging means is provided that comprises a means for selectively positioning an elongated ultrasound imaging head in a known position relative to the predetermined, three-dimensional frame of reference, including angulation of the ultrasound imaging head relative to the predetermined frame of reference. In the latter regard, the imaging head may be angled to image a layer, or "slice," of the body region of interest from a direction orthogonal to a direction from which an angled puncture instrument or other tissue-removal system may be advanced within such layer (i.e., the longitudinal axes of the imaging head and puncture instrument are parallel). Such ultrasound imaging allows for processor simulation/display of a biopsy procedure using a tissue-removal system from a given biopsy position, as well as real-time imaging/control of a biopsy device as it is actually advanced into the body region of interest.

In an additional aspect of the present invention, an ultrasound imaging means is provided that comprises a positioning means for supportably and selectively positioning an ultrasound imaging probe in known spatial relation to the predetermined, three-dimensional frame of reference, while also and alternatively allowing the ultrasound imaging probe to be disengaged from the positioning means and manually manipulated in hand-held procedures. More particularly, the positioning means may comprise a holder means for selectively receiving an ultrasound imaging probe that is also adapted for hand-held use, wherein the probe may be selectively employed for hand-held manipulation or alternatively positioned within the holder means (e.g., via sliding and/or "snap-in" engagement). In the later regard, the positioning means may be employed to supportably position the ultrasound imaging probe in predetermined relation relative to the predetermined three-dimensional frame of reference to obtain depth information in a desired layer, or "slice" of the body region of interest. Further, the positioning means may comprise one or more drive means for providing at least partial automated positioning of the ultrasound imaging probe (e.g., for automated X and/or Y dimension positioning and/or for automated rotational positioning about a Z axis within an XY plane).

As indicated above, x-ray images may be employed to select a limited, or targeted, portion of the x-rayed body region of interest to be imaged utilizing the ultrasound signal. Such targeted ultrasound imaging avoids the acquisition, storage and processing of unneeded imaging data, and otherwise facilitates efficient use of medical personnel time, and otherwise advantageously accommodates direct contact with the body portion to be imaged. Further, where necessary, the provision of a hand-held ultrasound imaging option provides practitioners with added flexibility as may be desirable in certain applications.

Additional features and advantages of the present invention will become apparent upon consideration of the further description provided herein.

DETAILED DESCRIPTION

Figure 1:
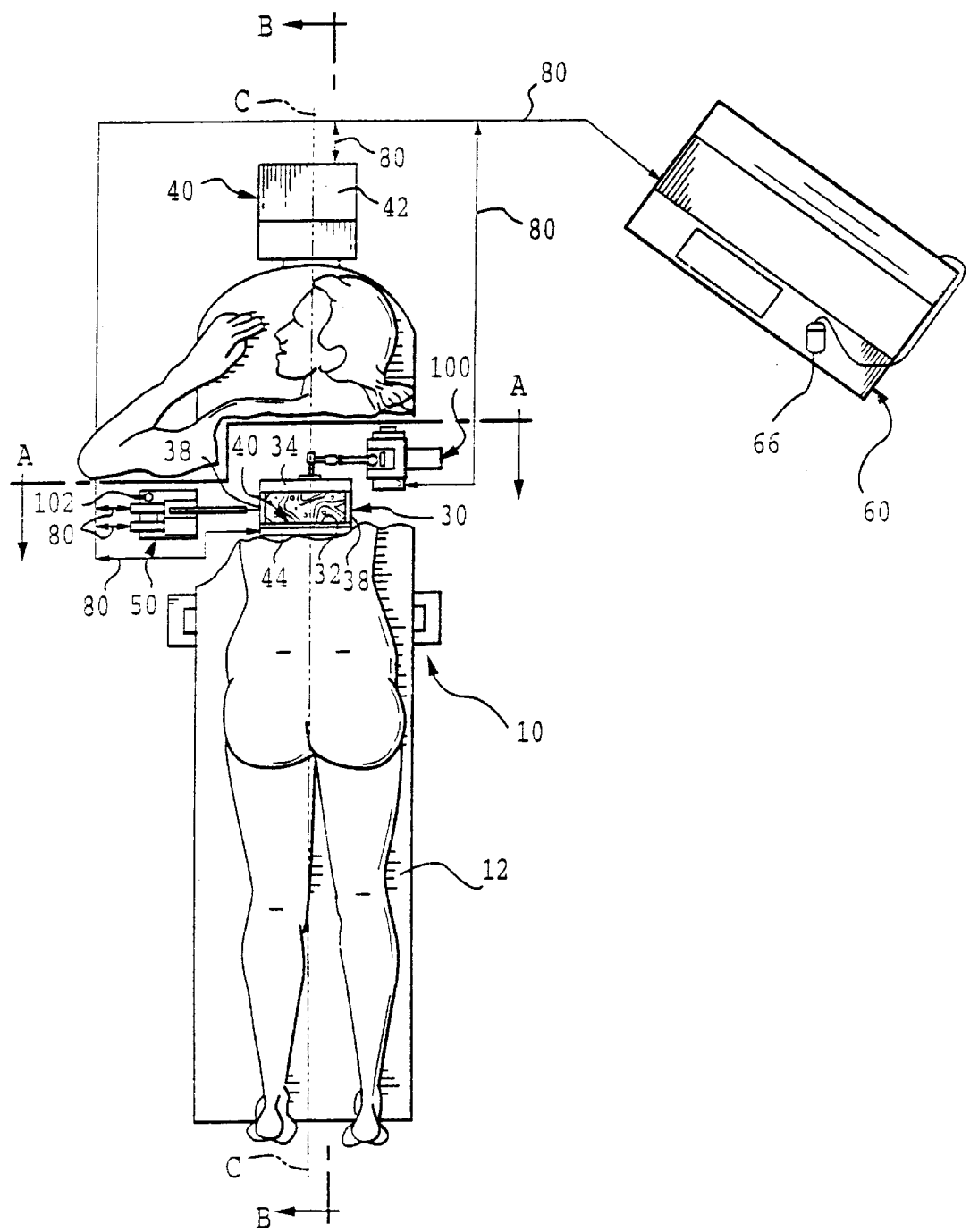
FIG. 1 is a top view of a stereotactic x-ray imaging system with integrated ultrasound imaging and biopsy components combinatively defining one embodiment of the present invention with a central patient/table portion cutaway to show key components.

FIGS. 1–6 illustrate one embodiment of a diagnostic ultrasound/x-ray biopsy system comprising the present invention, as adapted for mammography/breast biopsy use.

Generally, the system comprises a support assembly 10 having a patient table 12 with breast-opening 14 therethrough, an immobilization assembly 30 for immobilizing a patient's breast within a predetermined XYZ frame of reference under the opening 14 of table 12, an x-ray imaging assembly 40 for providing two-dimensional x-ray images (e.g., X-Y images) of the patient's immobilized breast in correlated spatial relation to the predetermined XYZ frame of reference, and an ultrasound imaging assembly 100 for providing orthogonal depth-profile images (e.g., X-Z, Y-Z and/or X,Y-Z images) of the immobilized breast in correlated spatial relation to the predetermined XYZ frame of reference. A biopsy assembly 50 having puncture instrument 52 is also provided for obtaining samples from a patient's breast while the breast is immobilized in the predetermined XYZ frame of reference. A display/processor assembly 60 is provided for recording/displaying the various images obtained/generated, for determining the coordinates of a user-identified location of interest within the breast and for monitoring/controlling/simulating the position of the various positionable assembly components.

As will be appreciated, the illustrated embodiment may utilize the x-ray, automated biopsy and other functionalities embodied in the current MAMMOTEST® and MAMMO-VISION® products of Fischer Imaging Corp. of Denver, Colo., U.S.A. In this regard, the present invention allows for the integration and effective use of ultrasound imaging with such products, thereby allowing medical equipment cost efficiencies to be realized. As noted previously, the MAMMOTEST® and MAMMOVISION® products include features corresponding with the disclosures in U.S. Pat. Nos. 5,078,142, 5,240,011, 5,415,169 and 5,735,264, which are incorporated by reference in their entirety.

Support assembly 10 further includes pedestal 16 and cantilevered first and second support arms 20 and 22, respectively, for supportably interfacing the breast immobilization assembly 30, x-ray imaging assembly 40, ultrasound imaging assembly 100 and biopsy assembly 50 in a predetermined spatially correlated manner. First and second supports arms 20 and 22 can be jointly pivoted relative to pedestal 16, thereby providing imaging/biopsy access to the breast from different directions (e.g., 0°, +90° and −90° relative to the table longitudinal axis). Additionally, second support arm 22 can be selectively pivoted relative to first support arm 20, to provide for stereotactic x-ray imaging (e.g., +15° and −15° relative to the first support arm longitudinal axis).

Breast immobilization assembly 30 is supported on first support arm 20 and includes a stationary face plate 32 and opposing compression paddle 34 for immobilizing a patient's breast therebetween. Compression paddle 34 is x-ray transmittent and further includes a window 36 for direct breast access by the ultrasound imaging assembly 100 and/or biopsy assembly 50. Compression paddle 34 is selectively positionable along first support arm 20 (e.g., via motorized and position sensor systems) for controlled, registered movement toward/away from face plate 32 to accommodate breast positioning/removal and differing breast sizes. Compression paddle 34 can be readily removed from/ interconnected to the first support arm 20 to accommodate the selective use of compression paddles of differing sizes, shapes, window positions, etc. As shown in FIG. 1, compression assembly 30 may further include selectively advanceable/retractable auxiliary side paddles 38, each having optional openings for breast access (e.g., by a puncture instrument or an ultrasound imaging head) for further compression/breast immobilization within the predetermined XYZ frame of reference, and particularly during use of biopsy assembly 50. In this regard, compression paddle 34 and face plate 32 are intended to define a breast imaging area of substantially common thickness and to immobilize such area during imaging/biopsy procedures, and to otherwise provide direct access to the breast for targeted ultrasound imaging/biopsy procedures.

X-ray imaging assembly 40 includes x-ray tube source 42 mounted on the end of second support arm 22 and x-ray receiver/imager 44 mounted on first support arm 20. As will be appreciated, x-ray tube source 42 provides x-ray radiation having a center axis C substantially perpendicular to the fronts of face plate 34 and x-ray receiver/imager 44, such x-ray radiation having a focal point positioned along the center axis C at a determinable location between the face plate 32 and compression paddle 34 during use. In this regard, and by way of example only, the predetermined XYZ frame of reference can be defined in the illustrated embodiment in relation to an X-Y plane corresponding with the front surface of the face plate 32 and/or parallel back surface of compression paddle 34, together with orthogonal X-Z and Y-Z planes within which the x-ray radiation center axis passes (i.e., all three planes being orthogonal). X-ray opaque markings (not shown) can be provided on compression paddle 34 and/or face plate 32 to facilitate spatial correlation of the radiation center axes and x-ray receiver/imager.

In the illustrated embodiment, the x-ray receiver/imager 44 is disposed in abutting relation with the face plate 32. X-ray receiver/imager 44 may comprise an image receptor consisting of a removable radiographic film cassette (e.g., for full-field breast imaging) and/or digital camera (e.g., for partial field, real-time imaging/display). In the latter regard, a partial field, digital CCD camera 46 (e.g., having a 5 mm×10 mm or 5 mm×5 mm imaging area) may be disposed for selective, driven XY movement (e.g., via a servo-drive arrangement) in registered relation to the predetermined XYZ frame of reference.

In the illustrated embodiment, ultrasound imaging assembly 100 and biopsy assembly 50 are selectively and alternatively connectable to opposing sides of first support arm 20 via connection/locking handles 102 and 55, respectively. Additionally, biopsy assembly 50 may be mounted in an axially aligned manner on first support arm 20 for breast access through window 36. A reference, or "home," position for each assembly in a given mounted location is known relative to the predetermine XYZ frame of reference. Further, positioning of the various components of each assembly during use is automatically determinable via position sensor/control systems. As will be appreciated, such positioning can be automated via corresponding processor-controlled, servo motors.

Biopsy assembly 50 comprises a punction sub-assembly 54, which includes puncture instrument 52, and positioner sub-assembly 56. Positioner sub-assembly 56 includes horizontal axis and vertical control motors 58 and 60, respectively, for selective sideward movement and upward angulation of the punction instrument 52. By way of example, punction sub-assembly 56 may comprise the AUTOGUIDE™ assembly of Fischer Imaging Corporation. As will become appreciated, the illustrated embodiment may be particularly apt for use with punction subassemblies for obtaining samples having relatively large cross-sections, including, for example, the MAMMOTOME™ from Biopsys Medical, Inc. of Irvine, Calif.

Ultrasound imaging assembly 100 comprises an ultrasound imaging head, or probe, 110 interconnected to arm assembly 130 and, in turn, to XYZ ultrasound positioning assembly 140. As will be further explained, XYZ ultrasound positioning assembly 140 is employed to selectively position ultrasound imaging head 110 through the window 36 of compression paddle 34 to establish direct breast contact for targeted ultrasound imaging in determinable spatial relation to the predetermined XYZ frame of reference.

Figure 5:
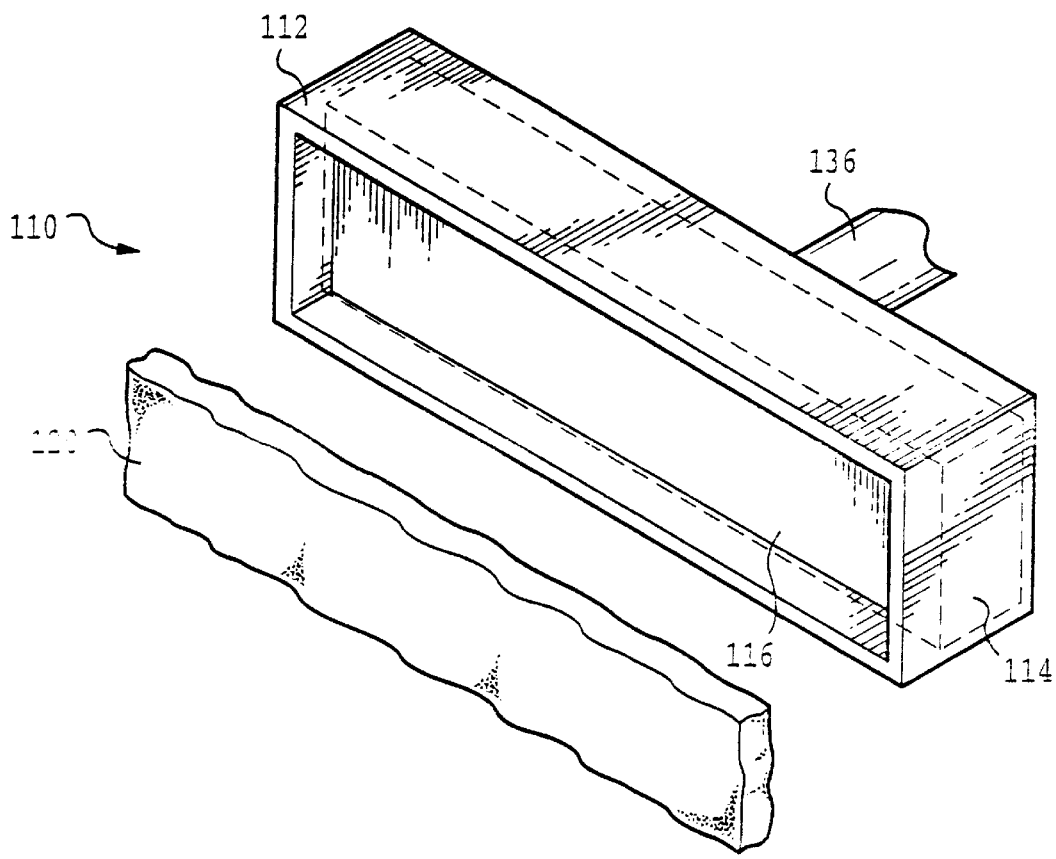
FIG. 5 is a perspective view of an ultrasound imaging head employable in the present invention.

As shown in FIG. 5, ultrasound probe 110 may include an elongated housing 112 with an elongated ultrasound transducer module 114 positioned therein. Ultrasound transducer module 114 provides an ultrasound signal having a focal point on a signal center axis at a location between compression paddle 34 and face plate 32. Ultrasound transducer module 114 may include, for example, a phased linear array of ultrasound transducers positioned along a longitudinal axis of the ultrasound probe 110. The ultrasound probe 110 emits signal pulses and detects corresponding echo pulses to generate the depth-profile images. More particularly, and as will be appreciated by those skilled in the art, detected echo pulses will result from ultrasound transmissivity differences (i.e., ultrasound impedance mismatches) at tissue-type transition areas (e.g., transitions between healthy tissue and a potential lesion/suspicious mass) and at structural obstructions (e.g., the front surface of face plate 32). The housing 112 of ultrasound probe 110 may include a recess 118 (exaggerated in FIG. 5) for receiving a cold-pack 120 for orthogonal application to a biopsy site after a biopsy procedure. Applying pressure and a cold medium directly over a biopsy site in the breast has been shown to reduce hematoma bleeding and bruising.

XYZ ultrasound positioning assembly 140 includes X, Y and Z platforms 142, 146 and 148, respectively, mounted for selective, registered movement on corresponding support members 152, 156 and 158 relative to the predetermined XYZ frame of reference. In this regard, XYZ positioning assembly 140 may include internal X, Y and Z optical position encoders. XYZ positioning assembly 140 can further include X, Y and Z motor drives for automatic, selective positioning of ultrasound imaging head 110 in registered XYZ relation to the predetermined XYZ frame of reference. The XYZ positioning assembly 140 may also include counterbalance and electro-lock components to accommodate ready manual positioning and to maintain a selected ultrasound imaging/biopsy position, respectively.

Arm assembly 130 is provided to allow the ultrasound imaging probe 110 to be rotated about one or more of selected X, Y and Z axes to obtain a desired pitch, roll and/or yaw orientation). For example, arm assembly 130 can be controlled to selectively rotate the longitudinal axis, or pitch, of probe 110 so that the ultrasound signal may be employed to obtain depth-profile image in a plane, or "slice," within which an upwardly angled punction instrument 52 of biopsy assembly 50 may be orthogonally advanced, as will be further discussed.

In the illustrated embodiment, arm assembly 130 includes pivot arm 132 pivotally interconnected to XYZ ultrasound positioning assembly 140 via a lock/release mechanism (not shown) for selective, centered rotation of probe 116 about axis YY. Arm assembly 130 further includes arm 134 rotatably interconnected to arm 132 via a lock/release mechanism (not shown) for selective, centered rotation of probe 116 about axis XX, and arm 136 rotatably interconnected to arm 134 via a lock/release mechanism (not shown) for selective, centered rotation of probe 116 about axis ZZ. Internal optical encoders (not shown) may be provided at the various arm interconnections, wherein the pitch, roll and/or yaw of probe 110 is automatically determinable in relation to the predetermined XYZ frame of reference. In this regard, internal automated micro-positioners may also be utilized under processor control.

As will be appreciated, the ultrasound signal may be scanned to obtain depth-profile information for a predetermined layer, or "slice," within the region of interest. By way of primary example, such scanning may be provided electrically by driving a phased linear array of transducers comprising probe 110 in a known manner and/or via manual or automatic-driven control of XYZ positioning assembly 140 to mechanically move ultrasound imaging head 110.

Figure 6:
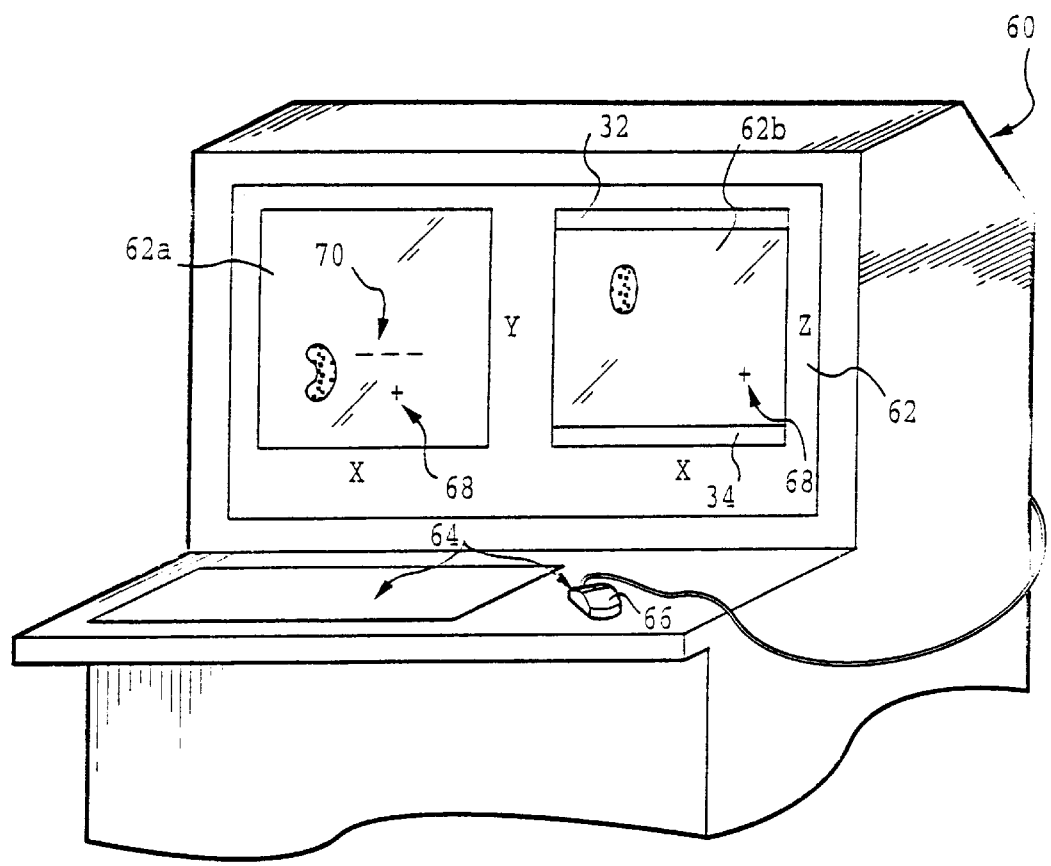
FIG. 6 illustrates spatially correlated x-ray and ultrasound images of a potential breast lesion/suspicious mass obtainable with the present invention.

As shown in FIG. 6, display/processor 60 includes a display screen 62 for displaying the acquired x-ray images on a first portion 62a and displaying corresponding depth-profile ultrasound images on a second portion 62b, each in registered co-relation to the predetermined XYZ frame of reference. Display/processor 60 may further include a user interface means 64, e.g., keyboard 65 and mouse 66 and screen point cursor 68 (e.g., on both display portions 62a, 62b), wherein a user may identify (e.g., click upon) a specific location-of-interest within both an x-ray image and corresponding ultrasound image (e.g., corresponding with a potential lesion or suspicious mass), e.g, for automatic processor determination of the three-dimensional coordinates of the location within the predetermined XYZ frame of reference. User interface means may further allow for user selection/display of a particular desired ultrasound depth-profile image, e.g., via mouse 66 and screen "slice" cursor 70 on the x-ray image display portion 62a. More particularly, screen "slice" cursor 70 may be employed to identify a particular slice, or layer, of an X-Y x-ray image for which a corresponding ultrasound depth-profile image is to be obtained (e.g., thereby resulting in processor-assisted positioning and imaging using probe 110) and/or accessed and displayed (e.g., where such ultrasound depth-profile image has been previously obtained/stored for selective subsequent review).

As indicated, display/processor 60 may be operatively interconnected (e.g., via electrical lines 80) to the various positionable assembly components for monitoring/controlling their respective positions relative to the predetermined XYZ frame of reference, including the positionable components of immobilization assembly 30, x-ray imaging assembly 40, ultrasound imaging assembly 110 and biopsy assembly 50. By way of primary example, display/processor 60 may determine the three-dimensional coordinates of a specific location of interest, as described above, and in turn assist/control the positioning of biopsy assembly 50 so as to position the assembly for obtainment of a tissue sample from the location of interest. In this regard, the display/processor 60 may also be employable to visually project, or simulate, the entry of a punction instrument 52 into a given location of interest, thereby allowing physicians the opportunity to insure an optimal positioning for biopsy entry prior to an actual biopsy procedure. Since three-dimensional visualization of a potential lesion/suspicious mass can be provided by the present invention, and since the disclosed arrangement allows for breast access by biopsy assembly 50 from a plurality of aspects (e.g., by selective mounting on either side of or coaxial along support arm 20), such simulated biopsy modeling may prone to be of particular advantage.

The present invention allows for spatial correlation of the x-ray and ultrasound images utilizing various techniques. By way of primary example, it can be appreciated that the X-Y x-ray images obtained can be readily correlated to the predetermined XYZ frame of reference since the position and attributes of x-ray source 42 and x-ray receiver/imager 44 are each known in relation to the predetermined XYZ frame of reference. Additionally, in stereotactic imaging procedures, the two X-Y stereotactic x-ray images can be employed to obtain a Z location for particular location of interest relative to the predetermined XYZ frame of reference utilizing known triangulation techniques, as will be appreciated by those skilled in the art. Further, the XYZ positioning of ultrasound imaging head 110 is determinable relative to the predetermined XYZ frame of reference, as noted above. Relatedly, in the embodiment described above, the ultrasound imaging head 110 will emit/detect ultrasound signals in substantially the same plane as the surface of compression paddle 34 contacting the imaged breast. The position of such surface relative to the predetermined XYZ frame of reference (e.g., the Z distance to face plate 32) is also determinable. In view of the foregoing, it can be seen that utilizing known ultrasound pulse/echo techniques a depth profile comprising a potential lesion/suspicious mass can be spatially related in a reliable manner to the acquired x-ray images.

In use, a patient can be positioned on the table 12 with a breast positioned through opening 14. Compression paddle 34 is then advanced along first support arm 20 to compress the breast to define a cross-sectional imaging area having a common thickness and to otherwise immobilize the breast in a set position within the predetermined XYZ frame of reference. X-ray imaging assembly 40 is then selectively positioned to obtain the desired x-ray images. Such x-ray images are then reviewed using display/processor 60, to identify, analyze and or otherwise confirm the presence and location of a potential lesion or suspicious mass for ultrasound imaging. Alternatively, the general location of a potential lesion or suspicious mass may already be known due to prior x-ray screening.

In either case, to proceed with ultrasound imaging, the patient should be positioned/repositioned so that the potential lesion or suspicious mass is positioned within the accessible field of view of ultrasound imaging head 110 when it is maneuvered through the window 36 of compression paddle 34 in direct contact with the imaged breast. As can be appreciated, in order for the present invention to yield spatially correlatable image information with respect to a potential lesion or suspicious mass, new x-ray and corresponding ultrasound images should be generated for each position in which a breast is immobilized within the predetermined XYZ frame of reference. As such, the benefit of utilizing a digital camera 46 in x-ray receiver 44 for partial field, real-time imaging via display/processor 60 can be readily understood.

Once it is verified that the area of interest is positioned adjacent to the window 36, ultrasound imaging probe 110 is positioned through the window 36 and a series of ultrasound images are obtained and displayed on display/processor 60. Cursor 66 control of the ultrasound images taken across the area of interest provides additional, valuable information as to the type of potential lesion/suspicious mass originally noted on an original mammogram. For example, with proper training of ultrasound and x-ray imaging techniques, physicians may rule out the possibility of a solid mass in favor of a fluid-filled cyst. Or, additional ultrasound characteristics may aid the physician in making a definitive diagnosis.

If it is determined that a biopsy is desired, the specific location from which tissue is to be obtained can be identified using mouse 66 to position screen point cursor 68 on both the x-ray image and correlated ultrasound depth-profile image on display/processor 60. Three-dimensional coordinates can then be determined and utilized by display/processor 60 to control positioning of biopsy assembly 50. In this regard, it will be appreciated that specific attributes of the particular punction subassembly 54 utilized will have been previously entered into by display/processor 60. Further, and as noted above, given such previous input information, display/processor 60 may be employed to simulate the advancement of punction instrument 52 into the breast from a given potential position, thereby allowing the physician to determine if breast biopsy access from a different position may be more desirable.

Figure 2:
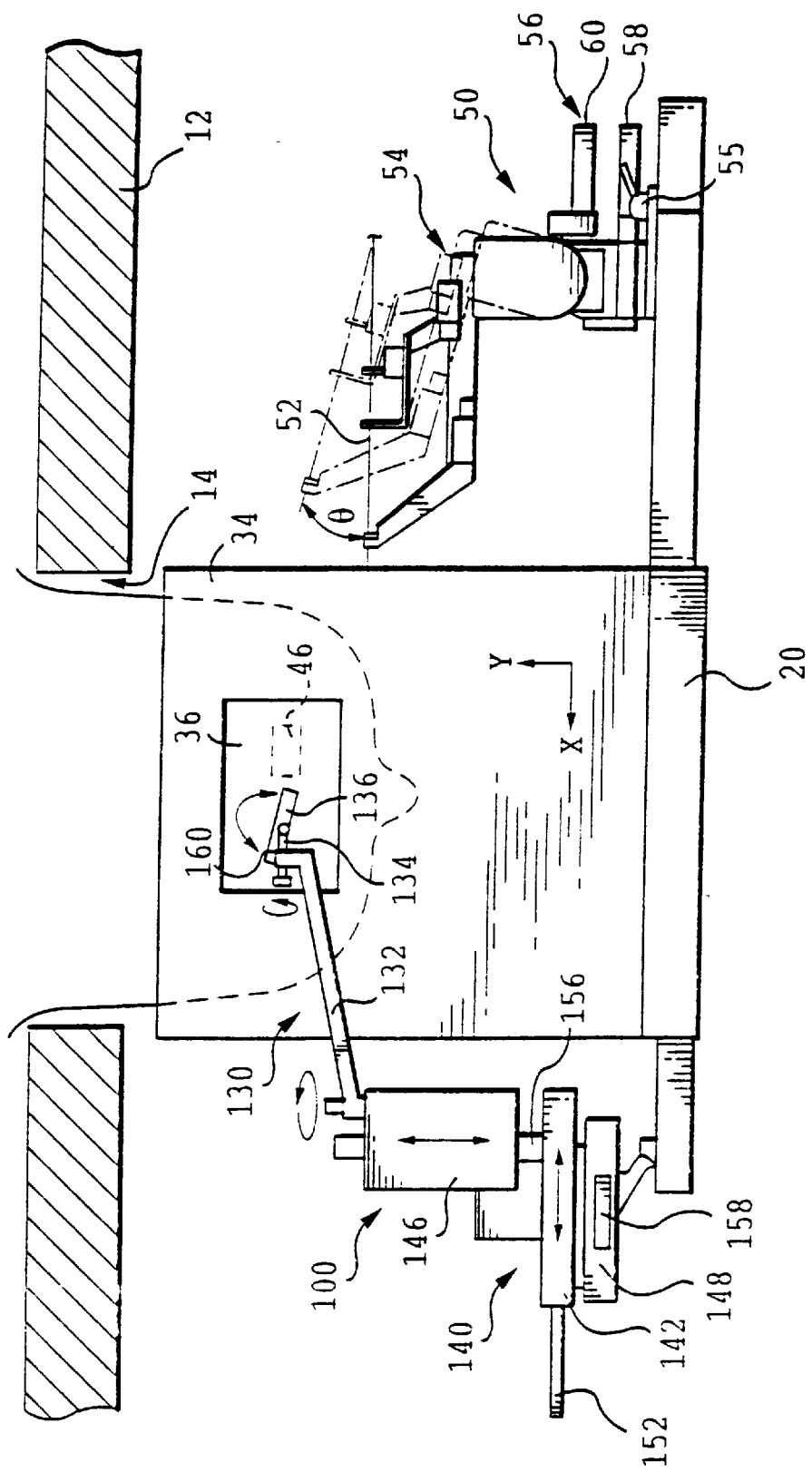
FIG. 2 is a partial end cross-sectional view of the embodiment of FIG. 1 cut along AA.
Figure 3:
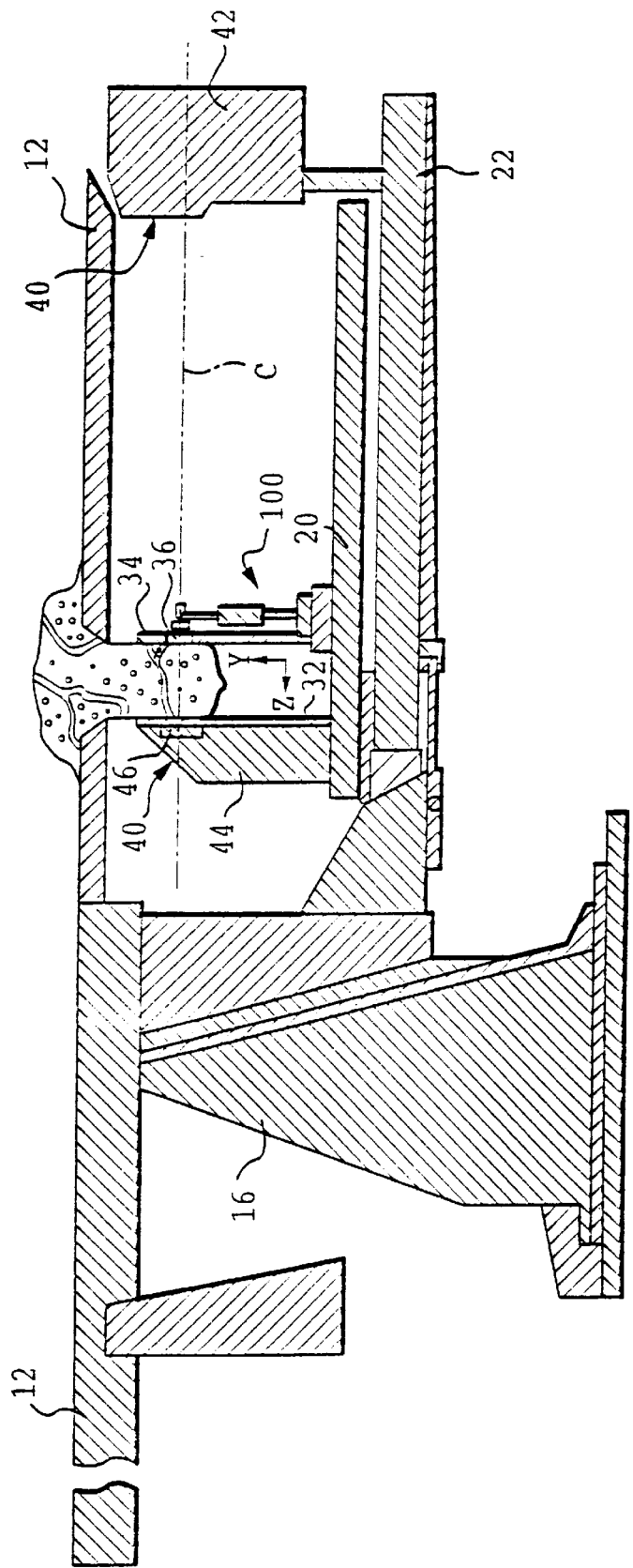
FIG. 3 is a partial side cross-sectional view of the embodiment of FIG. 1 cut along BB.
Figure 4:
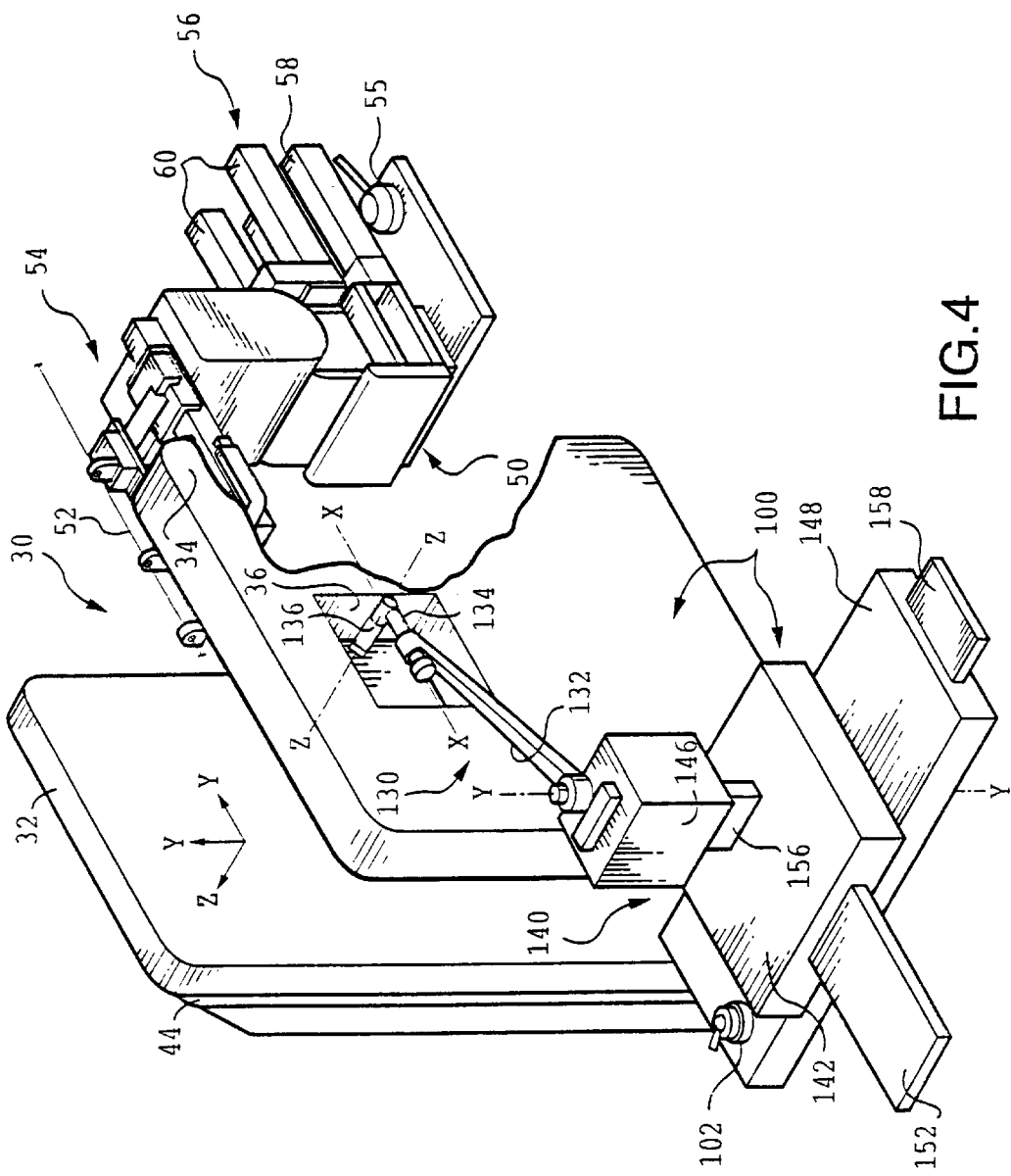
FIG. 4 is a perspective view of the immobilization, ultrasound imaging and biopsy assemblies of the embodiment of FIG. 1.

After the biopsy subassembly 50 is positioned as desired, biopsy procedures may be completed. In conjunction with such procedures, the ultrasound imaging head 110 may be utilized to provide continuous, successive depth profile images, thereby allowing for real-time monitoring and user control of the advancement of the punction instrument 52 into the breast. More particularly, when the punction instrument is positioned at an angle $\theta$ as illustrated in FIG. 2, ultrasound imaging head 110 may be similarly angled at $\theta$ (e.g., relative to horizontal) so as to yield real-time ultrasound depth-profile images of the layer into which punction instrument 52 is advanced. After biopsy procedures are completed, ultrasound imaging head 110 may be repositioned so as to allow for pressure application of a cold pack 120.

Figure 7:
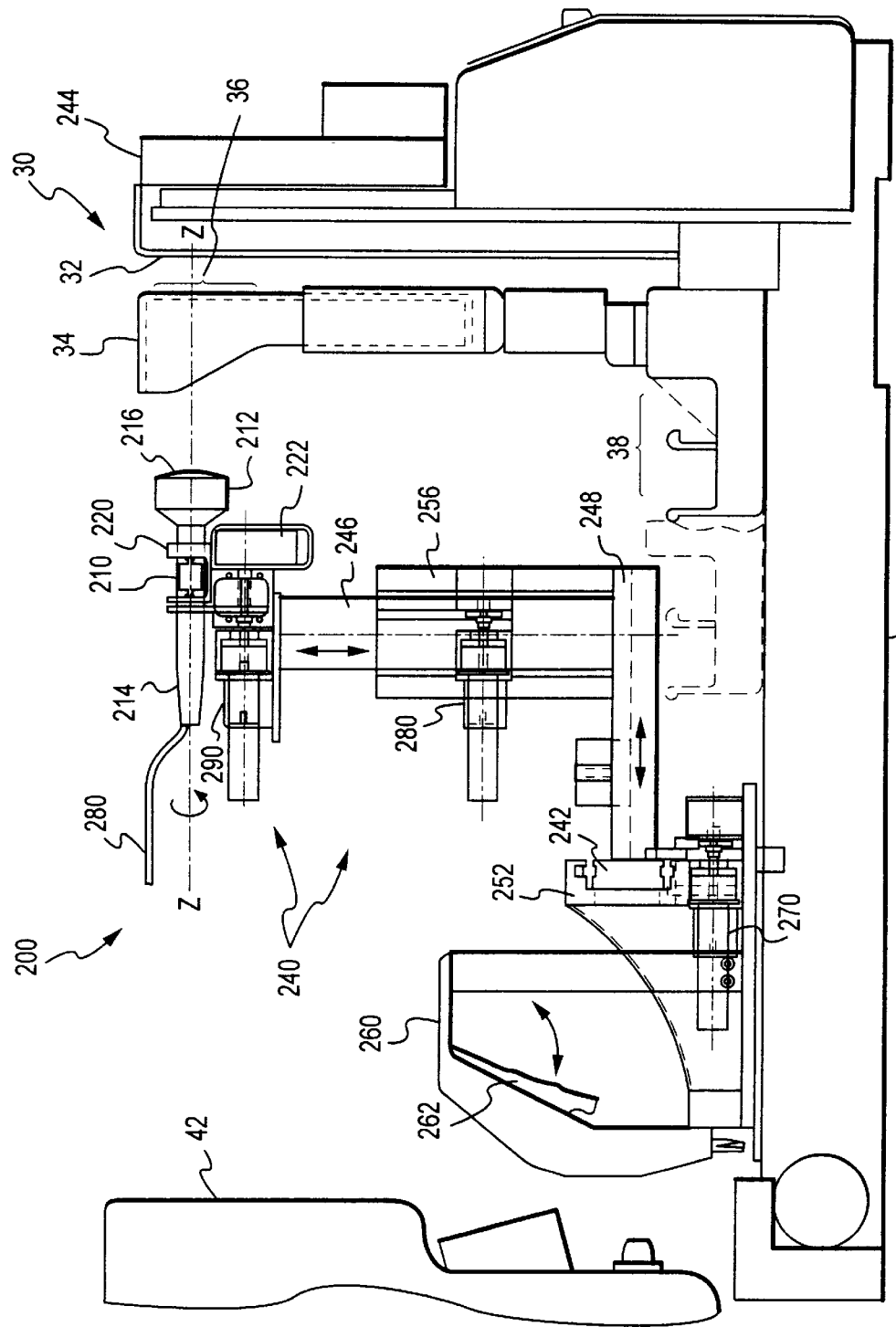
FIG. 7 illustrates a side-view of an alternative embodiment of an ultrasound imaging assembly comprising the present invention.
Figure 8:
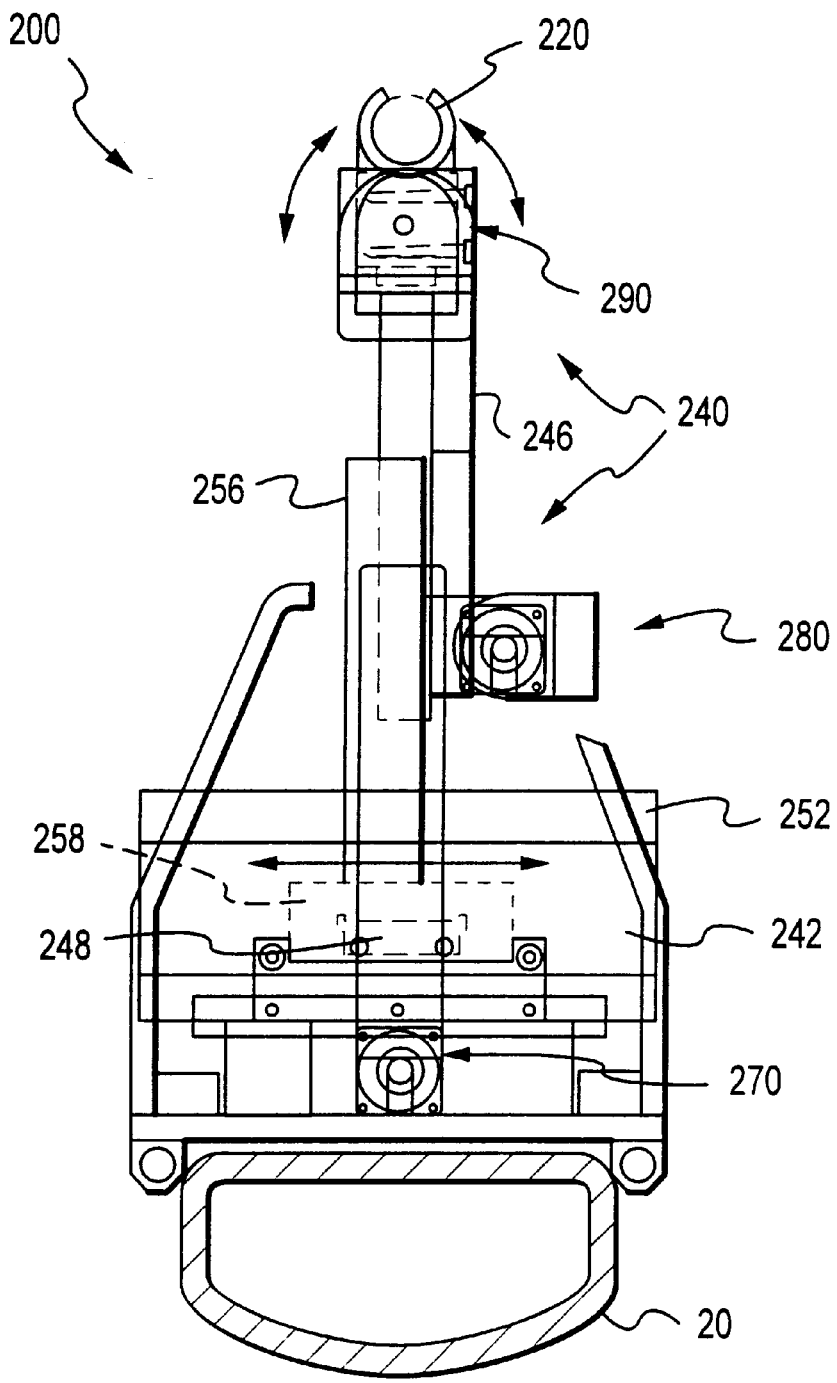
FIG. 8 illustrates a partially cut-away end view of the alternate ultrasound imaging assembly embodiment of FIG. 7.

FIGS. 7 and 8 pertain to an alternate embodiment of an ultrasound imaging assembly 200. In this regard, it should be noted that while the ultrasound imaging assembly 100 described hereinabove is supportably positioned below and on one side of a center axis of patient table 12, the alternate ultrasound imaging assembly 200 is provided to be supportably positioned immediately below and in substantial coaxial alignment with patient table 12. Such positioning of the ultrasound imaging assembly 200 allows for the alternate positioning of a biopsy assembly 50, as described above, on either side below patient table 12, thereby yielding enhanced access to the above-noted predetermined XYZ frame of reference.

As illustrated in FIGS. 7 and 8, the ultrasound imaging assembly 200 is supportably positioned on and in coaxial relation to the first support arm 20. First support arm 20 also carries breast immobilization assembly 30. As with the embodiment described above, the breast immobilization assembly 30 includes a stationary face plate 32 and opposing compression paddle 34 for immobilizing a patient's breast therebetween. Compression paddle 34 again is x-ray transmittent and includes a window 36 for direct breast access therethrough by the ultrasound imaging assembly 200 and/or a biopsy assembly 50. Compression paddle 34 is selectively positionable along the first support arm 20. In this regard, a locking mechanism portion 38 of compression paddle 34 is sized in the embodiment of FIG. 7 for positioning under at least a portion of ultrasound imaging assembly 200 to yield overall enhanced access and compactness advantages.

Support arm 20 may also support an x-ray image receiver/imager 244 positioned in opposing relation to the x-ray tube source 42. Image receiver/imager 244 may comprise a removable radiographic film cassette and/or digital CCD camera assembly for partial or full-field, real time imaging. In the later regard, receiver/imager 244 may comprise a CD assembly for full-field imaging as described in U.S. Pat. No. 5,526,394, hereby incorporated by reference.

With further respect to ultrasound imaging assembly 200, the assembly includes an ultrasound imaging probe 210 having an imaging head 212 (e.g., comprising an ultrasound transducer and/or linear array of transducers positioned at the end of an elongated handle portion 214. The handle portion 214 is configured for selective grasping during hand-held use and alternatively for positioning within a holder 220 having a cradle-like configuration. In the illustrated embodiment, the holder 220 includes two interconnected and aligned unshaped portions for conformally receiving a cylindrically shaped probe handle 214 (e.g., via "snap-in" and/or slide-in engagement). As will be appreciated, probe handle 214 and holder 220 may include projections and receiving slots or other means for establishing a predetermined positional relationship therebetween when engaged. The probe 210 may include an interconnect line 218 for transferring image data to a display/processor 60. For positioning relative to the predetermined XYZ frame of reference, holder 220 is mounted to an XYZ positioning assembly 240.

The XYZ ultrasound positioning assembly 240 includes X, Y and Z platforms 242, 246 and 248, respectively, mounted for selective, registered movement on corresponding support members 252, 256 and 258 relative to the predetermined XYZ frame of reference (i.e., defined between compression paddle 34 and face plate 32). The entire assembly 200 may be selectively removed from/interconnected to the support arm 20 utilizing a carrier assembly 260 having a depressible hand grasp 262 for retracting/advancing a locking pin(s) that interfaces with one or more openings along support arm 220.

Ultrasound imaging assembly 200 further comprises a first motor assembly 270 for driving X platform 242 for automated side-to-side movement of probe 210 in the X dimension. Similarly, ultrasound imaging assembly 200 also comprises a second motor assembly 280 for automated driving of platform 246 for up/down positioning of probe 210 in the Y dimension. Positioning in the Z dimension may be established by moving platform 248 relative to support member 258. Ultrasound imaging assembly 200 also includes a third motor assembly 290 for rotational movement of the holder 220, and in turn probe 210 mounted therewithin, about the axis ZZ. In this regard, holder 220 includes a microencoder for establishing the particular desired rotational angle of the ultrasound imaging probe head 212 (i.e., and the transducer and/or transducer array thereof) relative to the ZZ axis within the XY plane defined by the face 214 of the probe 210.

While the present invention has been described in relation to one embodiment, it will be appreciated that the invention may be utilized in numerous additional embodiments and procedures. Such additional embodiments and procedures are within the scope of the present invention, as defined by the claims which follow.

What is claimed is:

1. A medical apparatus, comprising:
    patient support means for supporting a patient such that a body region of interest of said patient is disposed within a predetermined, three-dimensional frame of reference;
    biopsy means, supportably mounted in a predetermined relation and moveable relative to said patient support means, for advancing into said body region of interest positioned within said predetermined, three-dimensional frame of reference at a selected entry angle relative to said three-dimensional frame of reference; and
    ultrasound imaging means, supportably mounted in a predetermined relation to said patient support means and positionable in direct contact with said body region of interest, for directing an ultrasound signal into said body region of interest to provide ultrasound image data corresponding with a depthwise profile of a plane passing through a portion of said body region of interest, said plane corresponding to a particular position of an ultrasound transceiver of said ultrasound imaging means, wherein said ultrasound imaging means is pivotably mounted relative to at least one axis passing through said ultrasound imaging means such that said plane of said body region of interest with which said ultrasound image data corresponds has a predetermined relation relative to said entry angle of said biopsy means.

2. A medical apparatus as recited in claim 1, further comprising:
    display means for displaying said ultrasound image data, wherein said ultrasound image data may be used in real time for guiding the advance of said biopsy means into said body region of interest.

3. A medical apparatus as recited in claim 1, wherein:
    said biopsy means includes:
        a puncture instrument; and
        puncture instrument positioning means for selectively positioning said puncture instrument at said entry angle relative to said predetermined, three-dimensional frame of reference; and
    said ultrasound imaging means comprises:
        an ultrasound imaging probe for directing said ultrasound signal into said body region of interest; and
        ultrasound imaging probe positioning means for selectively positioning said ultrasound imaging probe in contact with said body region of interest and selectively pivoting said ultrasound imaging probe about an axis passing through said ultrasound imaging probe such that said plane passing through said portion of said body region of interest with which said ultrasound image data corresponds has said predetermined relation relative to said entry angle of said biopsy means.

4. A medical apparatus as recited in claim 3, wherein said patient support means comprises a patient table and said puncture instrument positioning means is positionable below and on either side of a center axis of a patient table having an opening through which said body region of interest is accessible and said ultrasound imaging probe positioning means is positionable immediately below and in substantial coaxial alignment with said patient table such that said body region of interest is accessible to said biopsy means from either side of said patient table.

5. A medical apparatus as recited in claim 1, further comprising:
    x-ray imaging means, mounted in predetermined relation to said patient support means, for transmitting x-ray radiation through said body region of interest and for providing two-dimensional x-ray image data corresponding with one or more x-ray images of said body region of interest and correlated to said three-dimensional frame of reference, wherein said x-ray image data and said ultrasound image data combinatively provide correlated, three-dimensional image data corresponding with said body region of interest.

6. A medical apparatus as recited in claim 5, further comprising:
    processor means for processing said correlated, three-dimensional image data to provide a displayable three-dimensional model of said body region of interest.

7. A medical apparatus as recited in claim 6, wherein said processor is employable to simulate entry of said biopsy means into said body region of interest prior to actual advancement of said biopsy means into said body region of interest.

8. A medical apparatus as recited in claim 5, wherein said body region of interest is a female breast, and the apparatus further comprises:

an immobilization means for immobilizing said breast between first and second compression members, said first compression member having an opening therethrough, wherein said ultrasound imaging means is selectively positionable through said opening to directly contact the breast.

9. A medical apparatus as recited in claim 8, wherein said x-ray imaging means comprise:

an x-ray source for providing said x-ray radiation; and an x-ray receiver for receiving x-ray radiation passing through said breast, said x-ray receiver being positionable immediately adjacent to said second compression member.

10. A medical apparatus as recited in claim 9, wherein said x-ray receiver comprises:

a digital camera selectively moveable and positionable within a plane fixed relative to said predetermined, three-dimensional frame of reference; and user display and interface means for user identification, using an acquired and displayed x-ray image, of an acquired ultrasound image to be displayed.

11. A medical apparatus as recited in claim 5, further comprising:

display means for displaying said x-ray and ultrasound images in registered correlation.

12. A method for use in performing a biopsy procedure, comprising:

using a patient support to support a body region of interest within a predetermined, three-dimensional frame of reference;

providing a biopsy means, supportably mounted in a predetermined relation and moveable relative to said patient support, for advancing into said body region of interest at a selected entry angle relative to said three-dimensional frame of reference;

ultrasound imaging said body region of interest with an ultrasound signal directed from an ultrasound imaging means supportably mounted in a predetermined relation to said patient support to obtain ultrasound image data corresponding with a depthwise profile of a plane passing through a portion of said body region of interest, said plane being determined by a particular position of an ultrasound transceiver of said ultrasound means, wherein said plane passing through said portion of said body region of interest with which said ultrasound image data corresponds has a predetermined relation relative to an entry angle relative to said frame of reference of a biopsy means supportably positioned in a predetermined relation to said predetermined, three-dimensional frame of reference; and using said ultrasound image data to guide, in real time, advance of said biopsy means into said body region of interest to obtain a biopsy sample from a location of interest within said body region of interest.

13. The method as recited in claim 12, wherein said ultrasound imaging step comprises:

contacting said body region of interest with an ultrasound imaging probe that can be selectively pivoted about an axis passing through said ultrasound imaging probe wherein said plane passing through said portion of said body region of interest with which said ultrasound image data corresponds has said predetermined relation relative to said entry angle of said biopsy means.

14. The method as recited in claim 12, wherein said using step comprises:

displaying said ultrasound image date on a screen for viewing by a user during advancement of said biopsy means into said body region of interest.

15. The method as recited in claim 14, wherein said screen is adjacent to said biopsy means such that said screen is within the view of the user while the user is within reach of said biopsy means.

16. The method as recited in claim 12, further comprising:

x-ray imaging said body region of interest with x-radiation to obtain two-dimensional x-ray image data corresponding with each of one or more x-ray images; and combining said x-ray image data with said ultrasound image data to generate a three-dimensional model of said body region of interest.

17. A method for use in performing a medical procedure, comprising:

positioning a body region of interest within a predetermined, three-dimensional frame of reference;

supportably mounting a biopsy device having a puncture instrument in known spatial relation with said frame of reference and below and on one of two sides of a center axis of a patient table having an opening through which said body region of interest is accessible;

supportably mounting an ultrasound imaging probe in known spatial relation with said frame of reference and below and in substantial coaxial alignment with said patient table such that said body region of interest is accessible to said biopsy device from either side of said patient table;

ultrasound imaging said body region of interest with an ultrasound signal directed from said ultrasound imaging probe to obtain ultrasound image data corresponding with a depthwise profile of a plane passing through a portion of said body region of interest, said plane corresponding to a particular position of an ultrasound transceiver of said ultrasound imaging probe, wherein said plane of said body region of interest with which said ultrasound image data corresponds has a predetermined relation relative to an entry angle of said puncture instrument relative to said frame of reference; and using said ultrasound image data to guide, in real time, entry of said biopsy puncture instrument into said body region of interest to obtain a biopsy sample from a location of interest within said body region of interest.

18. The method as recited in claim 17, wherein said using step comprises:

displaying said ultrasound image date on a screen for viewing by a user during advancement of said biopsy means into said body region of interest.

19. The method as recited in claim 18, wherein said screen is adjacent to said biopsy means such that said screen is within the view of the user while the user is within reach of said biopsy means.

20. The method as recited in claim 17, further comprising:

immobilizing said body region of interest between first and second compression members defining opposing sides of said frame of reference.

21. The method as recited in claim 20, wherein said first compression member includes an opening therethrough and said ultrasound imaging step further comprises:

positioning said ultrasound imaging probe through said opening through said first compression member and in direct contact with said body region of interest.

22. The method as recited in claim 17 further comprising:

x-ray imaging said body region of interest with x-radiation to obtain two-dimensional x-ray image data corresponding with each of one or more x-ray images; and combining said x-ray image data with said ultrasound image data to generate a three-dimensional model of said body region of interest.

* * * * *